US007613573B2

(12) United States Patent
Zhang et al.

(10) Patent No.: US 7,613,573 B2
(45) Date of Patent: Nov. 3, 2009

(54) PRICING OF THE IDENTIFICATION SERVICE BY A REGISTRY WHICH IDENTIFIES PROSPECTIVE DONORS HAVING PARTICULAR BLOODTYPES TO A REQUISITIONER

(75) Inventors: Yi Zhang, Hillsboro, NJ (US); Michael Seul, Fanwood, NJ (US)

(73) Assignee: Bio ( * ) Notice: Subject to any disclaimer, the term of this patent is extended or adjusted under 35 U.S.C. 154(b) by 225 days.

(21) Appl. No.: 11/412,667

(22) Filed: Apr. 27, 2006

(65) Prior Publication Data

US 2006/0205001 A1 Sep. 14, 2006

(51) Int. Cl.
*G01N 33/48* (2006.01)
(52) U.S. Cl. .......................... 702/19; 435/7.1; 435/372
(58) Field of Classification Search ........................ None
See application file for complete search history.

(56) References Cited

U.S. PATENT DOCUMENTS

2003/0154108 A1   8/2003   Fletcher-Haynes
2003/0177036 A1   9/2003   Oka
2004/0093238 A1   5/2004   Deakter

*Primary Examiner*—Carolyn Smith
(74) *Attorney, Agent, or Firm*—Eric P. Mirabel (57) ABSTRACT

Disclosed is a registry for candidate transfusion donors, which invokes an inventory management policy to create and actively manage lists of candidate donors in order to minimize imbalances between demand and supply across multiple regions and across multiple categories of donors and recipients. Together with a genotyping laboratory, the registry does targeted recruitment of prospective donors who are typed for a set of genetic markers relating to clinically relevant antigens including mutations of Human Erythrocyte Antigens (HEA), genetic variants of Rh, and possibly additional antigens such as HLA and HPA. The registry monitors incoming demand for transfusion antigen genotypes, preferably stratify the demand into a set of categories representing stable subpopulations, and will apply strategies, disclosed herein, to tune the composition of candidate donor lists to match the demand, thereby avoiding excess, and unnecessary, typing of candidate donors.

9 Claims, 2 Drawing Sheets

Organization and Operation of an Actively Managed Transfusion Network

Effect of Sample Size (n) on the Probability of Finding Cross-Matches in Homogeneous Population (Phenotype = Do(a+b-) in this case).

PRICING OF THE IDENTIFICATION SERVICE BY A REGISTRY WHICH IDENTIFIES PROSPECTIVE DONORS HAVING PARTICULAR BLOODTYPES TO A REQUISITIONER

RELATED APPLICATIONS

This application claims priority to U.S. application Ser. No. 11/092,420, filed Mar. 29, 2005.

BACKGROUND

The matching of an extended set of significant antigens (ExtendedMatch™) will minimize adverse transfusion reactions (see Hillyer et al., Blood Banking and Transfusion Medicine; published. by Churchill Livingston, Philadelphia Pa.) and other potential complications arising from allo-immunization. This is so particularly for patients receiving multiple transfusions who, as in the case of hemoglobinopathies, may otherwise become refractory to transfusion. However, the virtually exclusive current practice of invoking serological methods to determine antigen phenotypes, one at a time, creates considerable logistical and economic challenges for the effective implementation of this standard. Thus, the use of serological typing methods to identify large numbers of prospective donors with a desirable repertoire of major and minor transfusion antigens so as to support diverse inventories of blood products will require a substantial investment of both time and resources, especially given the increasing expense for increasingly rare serological reagents. Further, in part reflecting this investment, the cost of acquiring such units, typically priced to include a surcharge per desirable antigenic marker matched per unit, can be prohibitive. The procurement of matched blood for recipients, who either display an uncommon antigen or lack a common antigen, is particularly problematic. While collections of transfusion donors with rare minor blood group phenotypes have been initiated (see the Redcross website), they remain limited, for example with currently only 30,000 donors registered in the American Rare Donor program.

Recent technological innovation (Hashmi et al., Transfusion, 45, 680-688 (2005)) has the potential to enable the replacement of serological methods of transfusion antigen determination by methods of genetic analysis. These methods would not only obviate the need for rare and expensive serological reagents but also would permit the concurrent ("multiplex") analysis of an entire set of genetic determinants of transfusion antigen phenotypes. Large-scale multiplexed transfusion antigen genotyping, particularly when combined with non-invasive collection of samples such as "finger sticks" or buccal swabs, would provide a basis for rapidly surveying donors for an extended set of clinically significant antigens and to construct a diversified inventory prior to collecting, processing and storing blood products.

The concept of a candidate donor inventory previously has been implemented in the form of bone marrow donor registries which have been organized around the world to provide a diverse pool of candidate donors who can be genetically matched to patients by comparing the relevant genetic loci within the Human Leukocyte Antigen (HLA) complex. However, in view of the highly variable nature of the HLA gene complex, these registries, in order to ensure a finite probability that a request for a specific HLA type can be filled, must acquire and maintain a large inventory by "taking all comers" Yet, by the same token of genetic diversity within the HLA complex, the likelihood of any donor being called upon is small, repeat donation exceedingly rare, and inventory turnover low. In view of the substantial expense of recruiting and typing prospective bone marrow donors, the operation of such repositories in an economically viable manner is difficult at best, and in fact, generally requires public expenditure (as in the case of the National Marrow Donor Program, see their website) or private philanthropy (as in the case of private registries maintained by foundations around the world).

In contrast to bone marrow and organ donation, blood donation is relatively painless, and is performed in high volume, at an annual rate of approximately 50 million donations worldwide, routinely including repeat donation, creating high turnover in existing supplies of blood products. The introduction of large-scale genetic typing into transfusion diagnostics would permit a systematic increase in the diversity of the inventory to support an ExtendedMatch strategy in a practical and cost-effective manner. A diversified inventory in turn would permit the rapid selection of a donor for a recipient with known transfusion antigen genotype (TAG) by genetic cross matching (see U.S. application Ser. No. 11/298,763, incorporated by reference).

The selection of compatible candidate blood donors in response to requests posted to a registry of such donors would facilitate the timely procurement of compatible blood products. This would be desirable in order to improve the public health and to minimize the cost accruing in the health care system in the form of unnecessarily prolonged hospital stays and adverse clinical effects arising from the administration of incorrectly or incompletely matched units of blood products such as red cell or platelets.

The operation of a transfusion donor registry of diverse composition and "critical mass" in a commercially viable manner calls for an effective organizational architecture and for strategies of optimal inventory management that represent a departure from the passive repository concept.

SUMMARY

The invention discloses strategies for the creation and commercially viable operation of a diverse registry of candidate transfusion donors, preferably within a transfusion registry and exchange network (TRXN). As described herein, the registry invokes an inventory management policy to create and actively manage lists of candidate donors in order to minimize imbalances between demand and supply across multiple regions and across multiple categories of donors and recipients. The registry monitors demand and manages supply, preferably by forming a commercial alliance with (or by operating its own) genotyping laboratory, by targeted recruitment of prospective donors who are typed for a set of genetic markers relating to clinically relevant antigens including mutations of Human Erythrocyte Antigens (HEA), genetic variants of Rh, and possibly additional antigens such as HLA and HPA.

To permit the determination of actual strategies (or "policies"), of managing the registry's inventory under various conditions, the registry described herein operates as an actively managed buffer between the fluctuating demand and the procurement of supply by directed recruitment of candidate donors to be placed into the list(s). The registry will monitor incoming demand for transfusion antigen genotypes, preferably stratify the demand into a set of categories representing stable subpopulations, and will apply strategies, disclosed herein, to tune the composition of candidate donor lists to match the demand. Methods of stratifying demand into a set of known, stable subpopulations also are described, as are strategies for directed recruiting of prospective donors, preferably by way of non-invasive sample collection The demand, in the form of requests posted by member institutions for units needed instantly as well as in the form of units reserved for later use, generally will display regional imbalances and, at any one location, generally will fluctuate in time. The invention discloses strategies of operating the registry so as to maximize the probability of fulfilling the set of requests received at any one time—that is, to minimize the probability of failing to procure a set of donors who are genetically compatible with the set of requests—under the constraint of a preset budget.

Genotyping of prospective donors represents a principal contribution to the cost of operations. The identification, characterization and recruitment of donors with special and thus generally less common phenotypes (and corresponding genotypic attributes) requires special effort and corresponding expense, and fully characterized blood products from such donors generally command premium prices. It will be a specific objective of the registry to maintain a list of such special donors. To that end, certain strategies are disclosed for improving upon random sampling in identifying donors with special phenotypes by stratification of the donor population into stable sub-populations. The optimal desirable composition of the list(s) matching the anticipated demand across a set of categories dictates the fractional allocation of funds available for genotyping stratified subpopulations.

The registry disclosed herein generates revenue by issuing to its member institutions including hospital transfusion services and traditional donor centers, the "permission to call" specific donors. That is, a member institution can acquire the right to call upon a specific donor, for one or more blood donations over a specified period, and perhaps for specific application of derived blood products. Several arrangements and corresponding pricing options including the analog of license and royalty payments are disclosed. There is a "flat" pricing model for units selected under ExtendedMatch criteria in order to facilitate placement of such units to generally greater clinical benefit to the recipient. Further, there are methods of providing incentives to encourage repeat donations from donors with desirable TAG attributes, including equity participation and/or profit sharing by individuals or community organizations.

In addition, the registry gains revenue by charging fees for membership as well as for services such as searches applying cross-matching rules (U.S. application Ser. No. 11/298763, incorporated by reference) and for providing a forum for member institutions to trade the "permission-to-call" licenses among one another. Preferably, the registry also can provide access to linked inventories of linked inventories of typed units of donor blood ("actual" units) maintained by its member institutions, thereby creating a larger potential market for providers, and a larger product selection to users. In addition, the registry can offer ancillary services such as transaction management (see U.S. application Ser. No. 11/092420, incorporated by reference) including on-line "genetic cross-matching, to identify available ("callable") compatible donors on its list. Rules relating to the selection of compatible donors under conditions of varying stringency are disclosed in U.S. application Ser. No. 11/298763.

Revenue generation is determined by the probability of being able to match requests submitted to the registry reflecting the inventory policies of member institutions—which in turn reflect requirements from within a population of recipients of known genotype distribution and certain actuarial risk profile relating to the occurrence of accidents and need for surgical procedures. This probability in turn depends on the size and composition of the registry. Within the framework of dynamic programming, the evolution in time of candidate donor list(s) within this buffer is managed to reflect the events that affect the list composition, including: acquisition of new candidate donors, selected from the set of such genotyped donors accepted into the list; re-acquisition of donors released from "permission to call" agreements by member institutions; and placement of compatible or desirable (potentially compatible) donors into permission-to-call agreements with member institutions attempting to manage their own respective inventories; as well as the gradual loss of callable donors who become unavailable.

Preferably, the registry forms part of a transfusion registry network (TRN), in the form described, which would ensure effective communication, and would create an effective forum for exchange of products and services between providers ("sellers") and users ("buyers"), both members of the network. To maximize the clinical benefit of a transfusion registry network, particularly under a ExtendedMatch paradigm, the network must offer access to a diverse population of donors reflecting the wide range of genetic characteristics of a diverse population of recipients.

Glossary:
"List"=a list of active callable donors;
"Registry"=a list of active donors plus "dormant" but callable donor.
"Availability" means the exclusive right of use is available; in the other words, list is also the real-time inventory maintained at TRN IT department.
"Callable donor"=a collection of information of a donor including identity, address, callability, genotype, blood type, and other relevant information.
"Callability"=an indicator of a donor measuring his/her willingness to donor one unit of blood next time, $0<$capability$\leq 1$.
"Not callable"=a situation when a donor is not active for donation and removed from the "list", i.e., callability=0.
"Blood type"=a combination of the presence of antigens or the absence of antigens (antigen negatives) in donor's blood.
"Category"=a collection of people with stable fractions of sub-populations (ethnicities).

Category can be demographic, such as local community, or birthplace, or genotype such as HLA types, etc.

Parameters and Variables

Part 1: Cost Parameters I.
K=fixed cost to start a typing program (such as planning and setup fees).
v=frequency of a blood type.
$c^t$=typing cost per perspective donor (fixed).
$c^d$=typing cost rate per callable donor (varies depending on active management).
$c^r$=cost rate for initial acquisition costs.
$h^r$=additional holding cost rate for callable donor inventory at donor centers.
$p^r$=penalty cost rate for backorders at donor centers.

Part 2: Logistic Parameters
$\alpha$=discount rate (one period) of cash, $0\leq\alpha\leq 1$.
L=lead time of a typing program.

Part 3: State Variables.
u=one-period demand for callable donors, a nonnegative random variable.
$u^b$=one-period demand for blood units, a nonnegative random variable.
$w^d$=inventory level of callable donors in the List.

$x^r$=pooled inventory level of callable donors at donor centers.
$\mu=\langle u \rangle<\infty$.
$\mu^b=\langle u^b \rangle<\infty$.
$y^i$=outstanding typing program initiated i periods ago, i=1, ..., L.
$\tilde{y}=(y^1, \ldots, y^L)$.

Part 4: Decision Variables.
z=pooled order size from donor centers to TRN-registry.
y=internal request size from TRN-registry-IT to TRN-registry-Lab.

Part 5: Auxiliary State Variable.
$v^d$=echelon inventory held in the system, i.e., donor center pool and the TRN-registry. From this definition, the echelon inventory equals $$v^d x^r + w^d.$$

Part 6: Index.
n=the number of periods remaining until the end of the planning horizon.

Part 7: Some Constraints $$y \geq 0, z \geq 0, x^r + z \leq v^d + y^L.$$

Part 8: Cost Parameters II.
β=natural decay rate of one callable donor unit over one period, $0 \leq \beta \leq 1$.
γ=decay rate of one callable donor unit per usage, or per blood unit acquired, $0 \leq \beta \leq 1$.
ε=fraction of revenue payable from donor centers to registry per blood unit sold per callable donor unit held at donor centers.
η=fraction per excess callable donor unit the donor centers considered selling back to the registry.
$x_c$=critical callable donor inventory level, above which donor centers will consider selling a fraction of excess callable donors back to registry.
ρ=revenue from sells per unit blood at donor centers.
$\rho^b$=buy-back revenue per callable donor unit at donor centers.

DETAILED DESCRIPTION

Section 0: Managed Donor List and Management Policy—The Case of Identical Donor and Recipient Populations A problem in a registry as described herein is to determine the optimal size of a candidate donor pool (to maximize the probability of having a match with recipients, yet reduce the costs associated with typing candidate donors) within a single homogenous or at least stable ("fully stratified") population identical to that of the recipient(s). The solution, given a distribution of phenotypes—and that of the underlying transfusion antigen genotypes, the matching probability (under a specified compatibility criterion—either an exact match or a match under the relaxed matching criterion, where the donor does not express any antigens not expressed by the recipient; see gXM application)—a cross-match probability is readily calculated—this provides the basis for determining the optimal number of donors from the same population that best fulfills transfusion demand without costly excess screening.

Probability of finding at least n donors of a certain blood type (indexed by l or the l-th type) in a randomly sampled donor set from the said population $$Pr(x \geq n | N, f_l) = 1 - \sum_{j=0}^{n-1} \binom{N}{j} f_l^j (1-f_l)^{N-j}$$

where parameter N is the size of a donor sample and $f_l$ is the frequency the blood type. The summation is from 0 to n−1.

EXAMPLE I

Effect of Donor Set Size and Recipient Blood Type on the Probability of Finding at Least n Donors.

It is clear that screening donors adds cost, but also that under-screening can result in donors not being available to fill demand, which results in revenue loss. Thus, it is beneficial to balance and arrive at a minimum number screened, so as to reduce cost, but maintain adequate inventory.

EXAMPLE I

Illustration of Donor Sample Size Effect on Cross-Matching Probability in a Homogenous Population.

Figure 1:
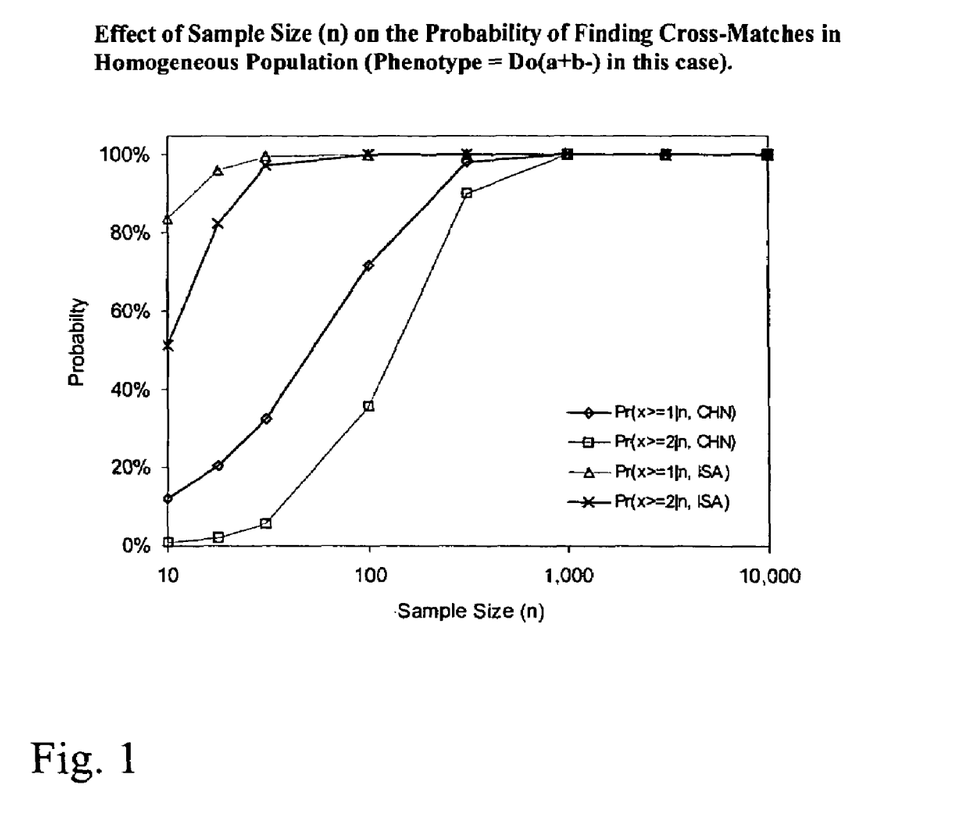
FIG. 1 depicts cross-matching probability of finding at least one and two phenotype-matched donors in two homogenous populations.

FIG. 1 illustrates the cross-matching probability of finding at least one and two phenotype-matched donors in two homogenous populations, Chinese and Israeli. One particular phenotype—Do(a+b−)—is considered in this example. Occurrence frequencies of this phenotype in Chinese and Israeli populations are respectively 1.26% and 16.56%. Those frequencies were determined by genotyping a number of donors. Obviously the more abundant the phenotype in a population, the higher the chance of finding matches; and, the larger the sample size, the higher the chance.

Probability of fulfilling a set of requests from recipients randomly selected from a given homogeneous (or "stable") population, as a function of the size of a donor pool randomly selected from the same population $$Pr(FF_l) = Pr(x_r \leq x_d | N_r, N_d, f_l)$$
$$= 1 - \sum_{i>j} \binom{N_r}{i} \binom{N_d}{j} f_l^{i+j} (1-f_l)^{N_r+N_d-i-j}$$

where $N_r$ and $N_r$ are recipient sample size and donor sample size, respectively, and $f_l$ is the frequency of the l-th blood type.

Active inventory management is the practice of matching inventory to average anticipated demand (as opposed to blindly maximizing inventory, thereby ensuring that requests will be met with high probability, but reducing turn-over, thereby incurring a low return on the initial investment of gTyping an excess number of candidate donors), which leads to the optimal solution. Maintaining inventory at a certain preset multiple of anticipated average demand is most desirable.

Demand for particular bloodtypes will vary based on factors including the genetic distribution of the relevant blood group antigens in each local recipient population. Where increased demand for certain bloodtypes is anticipated, stratification of donor populations such that those representing a larger proportion of such bloodtypes are identified, can be used to maintain demand/supply balance.

Section I: Right-to-Call Pricing and the Value of Repeat Donors

Candidate donors with desirable transfusion antigen attributes—generally implying premium pricing of blood products—are particularly valuable as repeat donors since no additional genotyping is required—this concept is not part of current blood bank pricing policies. Thus, simply selling an assay permitting genotyping may under-represent the potential future value of information derived by application of the assay. On the other hand, excess cost will be incurred.

The solution is a "right-to-call" pricing model, connecting price and cost of operations, most notably the cost of genotyping, which is further connected to transfusion antigen genotype (TAG) frequencies in the population and other factors. This pricing model is distinct from current methods where pricing is based on irrelevant parameter—e.g., the number of antigen negatives, that discourages efficient registry management and utilization of resources.

The "right-to-call" pricing structure would typically include an upfront payment ("access fee"), a periodic payment for the continued (defacto exclusive) right to call, and a fee based on the fraction of recurring revenue from sales of blood products derived from a specific donor. In return for undertaking a screening program at its own expense, hence at its own risk, a registry can identify candidate donors with special attributes. In return for having made an investment and having accepted the risk, the registry, when conferring upon a producer or distributor of blood products the right to call upon such a donor, can charge an upfront ("access") fee, a fraction of all revenue derived by the producer or distributor from such a donor ("royalty") and a periodic payment while the producer or distributor—in accordance with its own inventory policy—holds the right to call upon said donor, said periodic payment reflecting the registry's inability to generate revenue from conferring to a third party the right to call upon said donor. The size of the periodic payment can be based on the loss of revenue otherwise generated in the form of an access fee and royalty payments charged to a third party (periodic payment must be sufficiently high to deter producer from simply "shelving" the callable donor).

As an alternative, donor centers may choose to sell excess inventory of callable donors back to the registry, allowing sharing of donor information, or may elect to list excess inventory for sale to other participating donor centers by way of transactions hosted by the registry.

Pricing and the Standard of Clinical Care

The Relationship Between Pricing Strategies and Standards of Medical Care.

It is clear that mismatches in some blood group antigens are more clinically significant than others (see U.S. application Ser. No. 11/298763). The more clinically significant antigens cannot be as readily mismatched. The price for obtaining blood which can match such antigens is related to the amount of effort required to obtain the product, which has to do with occurrence frequency of that product in the population. The intrinsic value of one callable donor unit is related to the amount of effort invested for searching. If a blood type is rare, the price is usually higher. The price $\rho_1$ of one unit of blood of type l is approximately $\rho_l \approx \rho_0 + \rho_1 v_l^{-q}$, where q is a constant and $0 \leq q \leq 1$. Before T periods later, when one callable donor unit is fully depreciated, the total potential value per such unit is:

$$\pi_l \approx c^r \epsilon \rho_1 T.$$

The cost per callable donor unit can be represented by:

$$c_l^d = c_l^d(y, \theta, C_{max}) = \frac{C^*}{\sum_l y_l \sum_i v_i^{-q}},$$

with nonnegative constant q specified above, and the price per unit capability is related to the cost per unit by some scaling factor plus a price offset which can be either markup or markdown in order to match a demand curve:

$$p_l = k \cdot c_l^d + \text{offset}$$

Where bloodgroup determinants are typed in a "multiplexed" assay, which types a variety of bloodgroup determinants including those resulting in antigens having greater clinical significance, this avoids creating a disincentive to typing of antigens having greater clinical significance, as would occur in serotyping—where additional antigen typing can dramatically increase typing cost.

Section II: Active Management of a Donor Registry by "Optimal Mixing" Problem: as demand for blood fluctuates over time (that is, from period to period), imbalances may develop between demand and supply—random sampling becomes ineffective, because random donor sample may not reflect the actual blood type distribution in the demand and thus cause overtyping of donors and waste of resources. In addition, geographical imbalances between demand and supply will exist that remain stable over time.

Having introduced the concepts of a guided selection of candidate donors, and conferring a right to call upon available ("qualified") candidate donors and right-to-use fees, for the special case of a fully stratified population, it is now helpful to generalize to a situation, encountered in practice, characterized by an imbalance between the number of requests received per period from within a specific category ("fluctuating demand"), and the number of callable donors from within that category available to match those requests. The optimal strategy for active management of a registry in handling imbalances in "same-category" demand and supply calls for "optimal mixing" of candidate donor s selected from multiple available categories (e.g., African-Americans, Asians), each such category characterized by a set of antigens (and corresponding underlying transfusion antigen genotype) frequencies, and possibly other factors such as the readiness to donate.

Consider the function of the registry to maintain an actively managed list of candidate donors which is "not too small" and "not too large." In that list, each entry consists of the identity, genotype, and (corresponding) blood type of a donor, the blood type preferably in the form of a binary string representing the presence or absence of specific expressed transfusion antigens. (see gXM application). In addition, each entry also is assigned a "category" ("slot") which relates to the distribution of transfusion antigen genotype ("TAG") frequencies and related factors, such as actuarial factors, affecting the availability of candidate donors in that category. The numbers of callable (or active) donors in the slots represent the "inventory levels" at the TRN. Donors maintained in the list can also be inactive. Inactive donors can be those who are not available or reachable—these entries, after some time and in accordance with certain criteria—are removed from the active donor list or the inventory.

At any particular time, the number of requests from within a specific category may exceed the inventory of callable donors from within the same category. Maintaining an optimal inventory in such a situation calls for an optimal "mix" of candidate donors across multiple categories. A category, for example, can be a specific homogeneous population within the proximity of a specific blood bank client of the registry, or can be a demographic segment within a certain "stable" population (of known TAG frequencies). As discussed below, registry searches can be organized to return candidate donors per category, for example, availability at the nearest collection site.

The optimization problem relating to the general case is formulated in Section III by mapping it to the determination of the optimal inventory management policy for a 2-echelon model; it is shown that an optimal solution exists.

Section III: Operation of an Actively Managed Donor Registry

Often times, consulting the TRN may be more appealing for the immediate access to a greater selection of callable donors. For example, one donor center may "deposit" the availability of callable donors and an "order" requesting donor info of the same blood type can be "filled" via the network. Information sharing benefits both patients and service providers. Data centralization and "exchange" functionality of the TRN allows expansion of the network, and economies of scale will be readily assessable. The real-time aggregate demand and supply also provides the direct affiliates within the network a unique opportunity to forecast and better administer their donor recruiting programs.

III.1 Functional Organization

The TRN would actively managed the list ("buffer") between fluctuating aggregate demand in the form of pooled recipient requests and supply in the form of candidate donors recruited and TAG-typed at a laboratory, and would respond to specific requests from the list manager specifying optimal mixing ratios across specific donor categories.

Receiving and Processing Requests within a Network

A request for a particular blood product typically is initiated by a hospital on a patient's behalf The patient's genotype and so-derived blood type are sent to the donor center. If a matching unit is found in the donor center's own inventory of blood products, it is delivered. If no matching unit is found, the donor center subscribing to the services of a TRN (such as that disclosed in co-pending application Ser. No. 11/092420) may take one of two actions—it may look up a local list of callable donors and make arrangement for blood donation, or it may post a request for a unit of particular blood type on a listing hosted at the TRN.

All interested parties, including peer donor centers within the TRN, are able to view the listing and compete to fulfill the request, for example, by bidding (in accordance with an auction or other mechanism, see below) the winning donor center owns the right to deliver the unit. The mechanism of listing and bidding, preferably hosted at TRN's network site, such as a password-protected world-wide-web (WWW) site, facilitates competition and enables an efficient way of utilizing blood resources.

Donor centers, in order to replace blood units delivered in response to requests, may consult the registry to identify local callable donors and may elect to call upon such donors for donations.

Demand Monitoring by the List Manager

While fluctuations in demand at individual donor center may be large and random, the aggregate demand may display a smaller stochastic component. The reason is that, a hospital may choose to send request for a specific blood unit to any one of the available donor centers. If those centers are linked to a common registry network, demand fluctuations are distributed across the entire set of member institutions. Problem: predictability of demand fluctuation.

The solution is to pool demand by monitoring demand pattern in a centralized blood unit exchange. "Noise cancellation" would improve demand distribution prediction and facilitate development of optimal policy in inventory control. Callability is generally reserved for donors who have been genotyped but have not actually donated blood.

Replenishing the List: Donor Callability Status

This circle related to the handling and usage of blood product reduces "callability" of donors on the lists at donor centers. Again, the "callability" is an indicator measuring a donor's willingness to donate one unit of blood upon request. The value of capability is between 0 and 1. A value of zero means the donor is not callable and thus is removed from the list. If one adds up capability values of all donors in each category, the sum represents a measure of the level of a local inventory of qualified donors. If this level drops below some threshold, the center will attempt to replace the "spent" capabilities, by either identifying and typing qualified donors by itself or purchasing information units from a TRN of which it is a member.

A TRN, organized in accordance with the present invention, hosts an information-technology (IT) division which maintains a list of callable donors, provides cross-matching (xM) and bidding services to the donor centers, and generates requests for qualified donors. The TRN also has a relationship with a diagnostic laboratory, which directs selection of candidate donors and manages g-typing programs. The laboratory can be part of the TRN, for example, as a division, or it can be a TRN affiliate, funded by the TRN and/or other public expenditure.

Genotyping as a method of erythrocyte antigen typing and blood type determination makes it possible to separate—in time and in space—the processes of targeted recruiting of candidate donors; making the bloodtype determination (for example in an affiliated laboratory); and collecting and processing the actual blood;

The submission preferably takes place via an interface such as a website. Upon receiving a request, the user interface sends a request to the database management software at IT division of the TRN. The software looks up the active donor list, locates suitable donor(s) of the requested blood type(s), and then returns the information for downloading.

---

III.2 Transactions- flowchart
III.2A Typical 2-Party Transaction:
   Requesting Entity (location A):
   TheRegistry
III.2B 3-Party Transaction without Delay:
   Requesting Entity (location A):
   TheRegistry (location B):
   Field Collection Unit (location A)
   Requesting Entity (location A):
      Receive or anticipate request for specific blood type(s)
      place request to REGISTRY for specific bloodtype -continued

```
TheRegistry (location B):
    receive and process request (via gXM Engine);
    IF MATCH in Actively Managed Donor List (AMDL)
    {
        notify donor;
        schedule collection (local Processing Entity, or Field Collection
            Unit);
        manage shipment of unit to Requesting Entity;
    }
    ELSE ("out of balance supply")
    {
        notify closest Field Collection Unit;
        trans-ship sample to selected genotyping partner;
        notify donor;
        schedule collection (local Processing Entity, or Field Collection
            Unit);
        manage shipment of unit to Requesting Entity;
    }
III.2B 3-Party Transaction with Delay ("scheduled delivery"):
    Requesting Entity (location A);
    TheRegistry (location B):
    Processing Entity (location A)
```

III.3 Operating an Actively Managed Donor List: Optimal Inventory Policy

An active donor list at TRN can be viewed as a separate "virtual" inventory operating in tandem with an inventory of all local lists combined.

The optimal inventory policy at the registry is designed to absorb fluctuations in demand, in the form of the aggregate of requests generated by donors centers within the network. The active donor list at the registry is maintained in accordance with the optimal inventory policy by the registry's IT division which forwards requests for typing of new candidate donors to the diagnostic laboratory affiliate which organizes typing programs in order to fill the requests.

Figure 2:
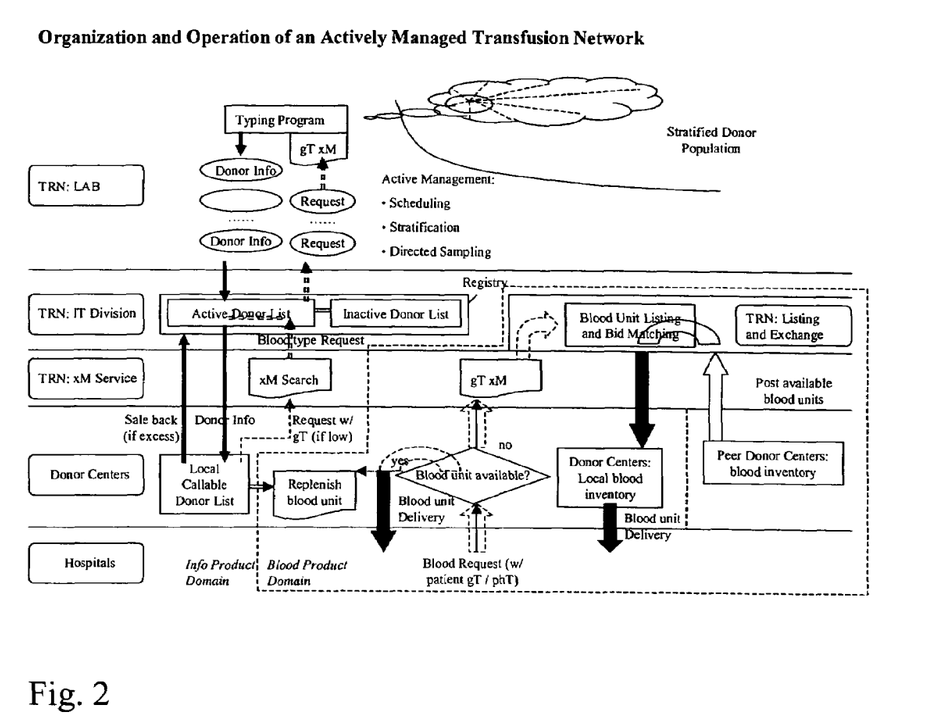
FIG. 2 depicts a scheme for organization of a transfusion registry network(s) (TRN), with hospitals, donor centers, patients and candidate donors, where the cross-matching of donors and recipients is carried out with genetic cross-matching (gXM) of genotypes.

To develop an optimal inventory policy for an actively managed registry handling the general case of demand-supply imbalance within the context of a network of interacting parties participating in the procurement of transfusion products, consider a registry as an element of a transfusion network. Such a transfusion network can be organized as illustrated in FIG. 2, comprising major entities including transfusion registry network(s) (TRN), donor centers, hospitals, patients and candidate donors.

Optimal Inventory Policy

A TRN preferably co-hosts listing and bidding services for blood unit exchange among the donor centers. Since the requests for callable donors reflects the requests for blood units after some time delay, a transfusion network may explore this correlation and improve its capability of predicting near-term overall demand for callable donors.

Actively Managed Buffer:

Inventory control coordinates demand (hospitals), retail inventory (donor centers), and warehouse inventory (registry) revenue. Best policy of recruiting and typing qualified donors depends on demand distribution, gXm, inventory levels, and cost per unit qualified donor unit quoted from affiliated lab.

Formulation of the optimization problem—minimize $\delta_{P \times M}$ at a given cost, and write down appropriate evolution equations to map onto dynamic programming and 2-echelon inventory models. (Buffers: blood center, registry).

Some Assumptions

To simplify an callable donor inventory at a donor center, we assume donor centers can always manage to replenish blood inventory level shortly after units are delivered before they further request donor contacts from a donor registry. Dynamics of inventory level at donor centers should also take into account the decrease in excess inventory due to the buy-back program at the registry.

Cost in the System

Suppose a donor registry serves more than one blood center, the pooled cost includes the fixed cost of subscription fee ($A^s$) and one-period expected penalty and holding (licensing) costs. If there is negligible variable cost of information delivery, the system-wide variable holding cost is negligible and only cost is penalty cost, that is $p^r E[u\beta x^r - z]^+$. Besides holding cost (licensing), other expected costs include initial acquisition cost and cost due to sales of blood unit drawn from the callable donors at hand (loyalty). The total expected cost is expressed as:

$$E([c^d(y, \theta, C_{max}) + \Delta]z + \varepsilon u^b) = [c^d(y, \theta, C_{max}) + \Delta]z + \frac{\varepsilon}{\gamma}\mu.$$

On the other hand, system-wide expected costs related to setup and typing acquisition A Finite-Horizon Dynamic Program A dynamic program, $\hat{g}_n(\tilde{y}, v^d, x^r)$, can be formulated to address minimum total discounted expected costs with n periods remaining, if the system begins from some initial state ($\tilde{y}$, $v^d$, $x^r$), excluding all the fixed costs.

Existence of Solution

Following footsteps of Clark and H. Scarf, "Optimal Policies for a Multi-Echelon Inventory" Problrm. Mgmt. Sci. 6, 475-490 (1960)., the problem is decomposed into a pair of sub-problems, which also makes it more relevant to the interest of donor centers. The first of the sub-problems involves donor center pool alone: Since $R(\bullet)$ is a convex function and adding a linear function of a function does affect the its convexity, a critical-number policy solves this problem.

From system's standpoint, neglecting the cost encountered between donor centers and TRN, which nets to zero, an induced penalty cost functions may be defined and a second dynamic program can be defined. Assume the demand probability distribution peaks, the penalty function should be a decreasing function of $\xi$ and set to zero as $\xi$ becomes greater than a critical level $x^r_n{}^*$. If the cost rate $c^d$ such that it does not affect the declining nature of the penalty cost at small y's, the minimization problem $\hat{g}_n{}^d(\tilde{y}, v^d)$ clearly is convex and an (s, S) optimal policy exists. Basically, shifting the initial acquisition cost appropriately to the loyalty charges later on facilitates the transactions between donor centers and the network and reduces the system-wide penalty of not filling requests from transfusion recipients.

The general minimization problem is now decoupled into sum of two sub-problems that are solvable:

$$\hat{g}_n(\tilde{y}, v^d, x^r) = \hat{g}_n{}^r(x^r) + \hat{g}_n{}^d(\tilde{y}, v^d),$$

and an optimal policy for the system consists of an optimal policy for $\hat{g}_n{}^d(\tilde{y}, v^d)$ for the typing programs and a modified critical-number policy for $\hat{g}_n{}^r(x^r)$ as the order policy from the donor centers.

The above formulation was derived for one blood type inventory and the budget constraint $C_{max}$ aims at a single blood type. In reality, many blood types coexist in the inventory. The above formulation is still valid in this case, except $C_{max}$ then stands for the budget constraint for typing programs attempting to find qualified donors of more than one blood type. The parameter $\theta$ will be introduced in the next section, which is related to the knowledge of stratified donor population. It will be seen the effect of the budget is reflected in the cost per callable donor, $c^d$, which takes part in the overall optimization of the current inventory control.

In a more general case: fluctuating demand from complex time-varying population→inventory control alone is not sufficient because demand distribution can greatly differ from any homogenous distribution→call for active management on supply side.

Active Management of Supply: "Optimal Mixing"

Problem: how to enhance representation of callable donors in view of fluctuating policies of heterogeneous nature resulted from inventory control?

Solution: selecting candidate donors and tuning inventory to minimize per callable donor cost by active mixing of at least two populations (and typing based on a mixing ratio). The goal is to minimize overall cost per unit callable donor, $c^d$, an implicit parameter in active demand management, related to the typing policy, categories, and a budget constraint: $c^d = c^d(y, \theta, C_{max})$, by way of directed sampling on the supply side.

The first step is to gain as much information as possible of the populations at hand. This step basically is to study the composition in the donor populations or, in the other words, to "stratify" a stable population into finer subpopulations, such as "pure" ethnicities or any other relevant stable categories.

Knowing the BloodType Distributions is a Prerequisite

In donor populations, bloodtype distribution is a prerequisite and the only way to arrive at an accurate result is by way of genotyping, so that a registry network has thoroughly collected information about the donor population. First of all, genotype frequencies of the sub-populations (ethnicities) are known, which are denoted by $\{f_{jl}\}$ with index l for different genotypes and j for different sub-populations. The summation of $\{f_{jl}\}$ over all genotypes for any given sub-population is thus unity, or $$\sum_l f_{jl} = 1.$$

We define ethnicity profile, which has been surveyed, for each category, indexed by i, as a set of mixing coefficients $\{c_{ij}\}$, which satisfies $$\sum_i c_{ij} = 1.$$

Since the frequency of occurrence of bi-allelic combination is additive, one can calculate the genotype frequencies in any given category by way of linear combination. We denote such frequencies with $\{\theta_{il}\}$ and the whole set with $\theta$. There is then $$\theta_{il} = \sum_j c_{ij} f_{jl}.$$

The frequencies of the sub-populations are time-invariant and the frequencies of the categories may vary slowly over time but can be monitored closely. Those observables are assumed known and not tunable. However, if sufficient genotype distribution in donor population is known, in principle, one can adjust the sampling strategy on the donor population so as to type and seek in the categories that are known to be richer in the genotypes of interest. Consequently, the overall typing cost of the qualified donors is lowered by directed sampling.

Formulate the Problem

We introduce $\{\omega_i\}$ to denote a set of mixing coefficients of the categories, or collectively by $\omega$. Let the mixed donor population be $\{v_l\}$. There is then $$v_l = \sum_i \omega_i \theta_{il} = \sum_{i,j} \omega_i c_{ij} f_{jl}.$$

Since the sampled population has uncertainty, we need to express the probability of completely filling (full-fill) of the requests ($y_l$). We denotes such probability $Pr^{ff}$ and there is $$Pr^{ff}\left(y_l|D, \omega, \theta\right) = \sum_{d_l \in [0,D]} \delta^{0+}(d_l - y_l) Pr(\xi = d_l|D, v_l),$$

where D is the total size of donor population and function $\delta^{0+}(\bullet)$ is defined as $$\delta^{0+}(y) = \begin{cases} 1 & y \geq 0 \\ 0 & y < 0, \end{cases}$$

Then, $$Pr^{ff}(y_l|D, \omega, \theta) = \sum_{d_l=y_l}^{D} Pr^{xM}\left(\xi = d_l \bigg| D, v_l = \sum_i \omega_i \theta_{il}\right)$$
$$= Pr^{xM}(\xi \geq y_l|D, v_l)$$

where $Pr^{xM}$ is a cross-match probability and can be approximated by a binomial distribution. The probability of fulfilling all $y_l$ requests of blood type l thus equals the probability of finding at least $y_l$ qualified donors in D individuals drawn from a mixed population, in which l-th blood type has a combined frequency of $v_l$. And the function has the form, $$Pr^{xM}(\xi \geq n|N, f) = 1 - \sum_{k=0}^{n-1} \binom{k}{N} f^k (1-f)^{N-k} \approx P(n, Nf),$$

which can approximated by an incomplete gamma function, $P(\bullet)$.

$$P(a, b) \equiv \frac{1}{\Gamma(a)} \int_0^x e^{-t} t^{a-1} dt = \frac{1}{\Gamma(a)} e^{-x} b^a \sum_{k=0}^{\infty} \frac{\Gamma(a)}{\Gamma(a+1+k)} b^k$$

The intrinsic value of one callable donor unit is related to the amount of effort invested to search for it. If a blood type is rare, the price is usually higher. The price $\rho_l$ of one unit of blood of type l is approximately $\rho_l \approx \rho_0 \rho_1 v_l^{-q}$, where q is a constant and $0 < q < 1$. Before T periods later, when one callable donor unit is fully depreciated, the total potential value per such unit is:

$$\pi_f \approx c^r + \epsilon \rho_l T.$$

The objective of the active management is to tune the sampling of donor population to minimize the probability of NOT realizing the full value of the potential callable donor units under given budget constraint. Such probability can be expressed as:

$$\delta_{P_r}^v(y|C, \omega) = \frac{\sum \pi_l[v_l(\omega, \vartheta)]y_l \cdot \left[1 - Pr^{\text{ff}}\left(y_l|D = \frac{C}{\bar{c}^t}, \omega, \vartheta\right)\right]}{\sum_l \pi_l[v_l(\omega, \vartheta)]y_l}$$

where $\bar{c}^t$ is the averaged cost over categories, if typing program adopts different configurations of the typing tools among the different targeted categories, then $$\bar{c}^t = \sum_i \omega_i c_i^t.$$

We denote optimal probability above $\hat{\delta}_{P_r}^v$ and define the following optimization problem:

$$\hat{\delta}_{P_r}^v(y, \theta, C_m, \delta_{th}) =$$

$$\min_\omega \left\{ [\delta_{P_r}^v(y|C, \omega) - \delta_{th}]^+ : C \geq 0, \omega \geq 0, \sum_i \omega_i = 1, C \leq C_m \right\},$$

where $\delta_{th}$ is a threshold in percentage, e.g., 0.1%, and $C_m$ is the maximum typing budget. If the optimal total cost is below this budget limit, the problem is to minimize $\delta_{P_r}^v$, or if possible to make it below the threshold $\delta_{th}$. Otherwise, the problem is minimization of $\delta_{P_r}^v$ under total cost constraint, $C_m$.

Prove Optimal Cost is the Lowest Cost

Let $\omega^*$ and $C^*$ be solution of the above optimization problem, namely, $\omega^*$ denoting the optimal mixing coefficients of categories and $C^*$ denoting the "optimal" cost. Intuitively, the so-calculated $C^*$ is "optimal" in the sense that it is the minimal cost of arriving at any given $\delta_{P_r}^v$. The proof is by contradiction. Suppose the optimal cost is not minimal cost for a given $\delta_{P_r}^v$, there should exist a total cost $C^{**}$ ($<C^*$) that achieve the same $\delta_{P_r}^v$. Then, instead of saving on the total cost by the net amount of $C^*-C^{**}$, we put it in use and type some extra prospective donors but concentrating on one existing category. The result: with the same $C^*$, we achieve a lower $\delta_{P_r}^v$ with an effectively different, obviously better, $\omega^{**}$. This contradicts our assumption that $\omega^*$ optimal.

The cost per callable donor unit can be then computed as:

$$c_l^d = c_l^d(y, \theta, C_{max}) = \frac{C^*}{\sum_l y_l} \frac{v_l^{-q}}{\sum_l v_l^{-q}},$$

with nonnegative constant q specified above. Interestingly, a smaller value of p shifts the cost from extremely rare blood types to less rare ones. By using appropriate pricing strategy, the system-wide utility efficiency can be lifted. The averaged cost per callable donor is:

$$\bar{c}^d = \bar{c}^d(y, \theta, C_{max}) = \frac{C^*}{\sum_l y_l}$$

Global optimization—an inventory model was formulated that handles demand fluctuation and non-zero delay in delivery of the typing results. We showed that optimal solutions exist to solve the inventory problem. However, the cost structure has to be decided together with the typing programs. We then formulated the optimization problem that finds the optimal mixing coefficients that best fulfills the request under budget constraints. This problem handles the uncertainty on the supply side, namely the donor population, by way of stratification and tuning. The best cost structure is then a negotiation parameter between the demand solution and supply solution. By solving two solutions iteratively, one can achieve global solutions.

In a case of an initial random mixed (patient) population, the optimization problem is likely end up with a set of mixing coefficients simply reflects the proportions in the mixing coefficients of ethnicities in the sample. As the registry operation continues, it is likely bloodtype distribution in the patient population follows a pathway so that real-time composition deviates unpredictably from the original one. In such case, a general global optimization routine should be run in order to reach an optimized mixture of donors and a system-wide low cost. An interesting case is unusually high occurrence of rare bloodtypes may be easily cross-matched by looking into a different ethnicity or in a different region, in which such types are more frequently represented—an action that is likely automatically taken by the optimization process.

It should be understood that the terms, expressions and examples herein are exemplary only and not limiting and that the scope of the invention is limited only by the claims which follow, and includes all the equivalents of the claimed subject matter.

What is claimed is:

1. A method of pricing by a registry which identifies prospective donors having particular bloodtypes to a requisitioner seeking to recruit such donors for blood donation, comprising determining, using a processor: expenses relating to recruiting candidate donors and determining their bloodtype, the number of candidate donors analyzed being chosen to ensure fulfillment of a preset fraction of the anticipated requests received, on average, per period of operation; the length of time during which donations by a selected candidate donor are, or can be, collected by a requisitioner; and proceeds generated by the requisitioner from sale of products derived from blood donated by a selected candidate; and adjusting the price charged by the registry for said identification to reflect: said expenses relating to recruiting; said length of time; and the proceeds generated from said sale of said products and wherein said price charged is output in a user readable format.

2. The method of claim 1 wherein the number of candidate donors are further selected such that the expenses relating to recruiting candidate donors to be analyzed do not exceed an upper limit.

3. The method of claim 1 wherein the bloodtypes comprise multiple phenotypes correlating with expression of antigens on human erythrocytes.

4. The method of claim 3 wherein the antigenic phenotypes are from major and minor blood group systems.

5. The method of claim 1 wherein the bloodtypes include Duffy, Dombrock, Landsteiner-Wiener, Colton, Scianna, Diego, Kidd, Kell, Lutheran and MNS.

6. The method of claim 1 wherein identifying candidate donors having a particular bloodtype comprises analysis of a designated set of genetic determinants for expression of antigenic markers defining the bloodtype.

7. The method of claim 6 further including analyzing said designated set of genetic determinants concurrently.

8. The method of claim 7 further including pricing blood products produced from donations by donors with desirable bloodtype such that the price of said blood products is independent of the number of matched determinants.

9. The method of claim 7 wherein revenue from the sale of blood products produced from donations by donors with desirable bloodtype is independent of the number of matched determinants.

* * * * *